United States Patent [19]

Stovicek

[11] Patent Number: 5,096,488

[45] Date of Patent: Mar. 17, 1992

[54] ANTIFOULING COMPOSITION

[75] Inventor: Pavel Stovicek, British Columbia, Canada

[73] Assignee: Waitomo Industrial Investments Ltd., British Columbia, Canada

[21] Appl. No.: 631,652

[22] Filed: Dec. 21, 1990

Related U.S. Application Data

[60] Division of Ser. No. 304,769, Jan. 31, 1989, Pat. No. 4,990,547, which is a continuation-in-part of Ser. No. 153,010, Feb. 8, 1988, Pat. No. 4,866,106.

[51] Int. Cl.$^5$ .................................................. C08K 5/19
[52] U.S. Cl. ............................. 106/18.32; 106/15.05; 424/405; 424/408; 424/500; 424/522; 523/122; 524/236; 428/255; 428/411.1; 428/537.1; 428/688
[58] Field of Search ............... 106/15.05, 18.32; 424/405, 408, 500, 522; 523/122; 524/236; 428/255, 411.1, 537.1, 688

[56] References Cited

U.S. PATENT DOCUMENTS

| | | | |
|---|---|---|---|
| 3,854,960 | 12/1974 | Plum et al. | |
| 4,128,429 | 12/1978 | Wyant et al. | |
| 4,273,833 | 6/1981 | DeLong | 523/122 |
| 4,631,302 | 12/1986 | Supcoe et al. | 523/122 |
| 4,661,400 | 4/1987 | Guglielmo, Sr. | 428/255 |
| 4,675,051 | 6/1987 | Baxter | 106/16 |
| 4,687,792 | 8/1987 | Russell et al. | 523/177 |
| 4,752,629 | 6/1988 | Proudlock et al. | 523/122 |
| 4,866,106 | 9/1989 | Pellow et al. | 523/122 |

FOREIGN PATENT DOCUMENTS

| | | |
|---|---|---|
| 53-124538 | 10/1978 | Japan . |
| 60-210677 | 10/1985 | Japan . |
| 60-217274 | 10/1985 | Japan . |
| 62-084167 | 4/1987 | Japan . |
| 62-232470 | 10/1987 | Japan . |
| 63-008462 | 1/1988 | Japan . |
| 63-081177 | 4/1988 | Japan . |
| 63-161041 | 7/1988 | Japan . |

*Primary Examiner*—William R. Dixon, Jr.
*Assistant Examiner*—Anthony J. Green
*Attorney, Agent, or Firm*—Darby & Darby

[57] ABSTRACT

An antifouling coating composition useful for coating fish netting, boat hulls, lumber, roof shingles and the like to prevent the growth of algae or fungi. The composition comprises a vinyl polymer or copolymer emulsion containing a dialkyldimethyl ammonium compound with or without an alkylbenzyldimethyl ammonium compound. The preparation of the composition must be done with care in order to prevent the added quaternary ammonium compound from destabilizing the emulsion polymer. The invention also relates to articles coated with the composition to prevent the formation of algae and fungi thereon.

7 Claims, No Drawings ns 5,096,488

ANTIFOULING COMPOSITION

This is a division of application Ser. No. 304,769, filed Jan. 31, 1989, now U.S. Pat. No. 4,990,547, which in turn is a continuation-in-part of application Ser. No. 153,010, filed Feb. 8, 1988, now U.S. Pat. No. 4,866,106, issued Sept. 12, 1989.

FIELD OF THE INVENTION

This invention relates to an antifouling coating composition. The composition is useful for coating equipment to be submerged in the sea, for example, fish nets and boat hulls, but also finds use for protecting and preserving lumber and roof shingles and the like exposed to much rain and subject to algae and fungal growth.

DESCRIPTION OF THE PRIOR ART

The growth of algae and fungus on structures, for example, on boat hulls, on fishing nets, on roofs, on patios and on lumber is unsightly. There are, however, more important failings. The hull of a boat is considerably less efficient when coated with algae; the drainage of a roof can be adversely affected by the presence of algae; and patios, balconies and the like can become slippery when wet if algae are present. In industry, fouling and plugging of water pipes, particularly in cooling systems, can occur with algae growth, for example, in the pulp and paper mill industries. The warm temperatures in cooling system waters make ideal conditions for algae growth.

A hull of a boat or a walkway can be scrubbed to remove the algae but, for example, in the case of a boat, this involves removing the boat from the water and also a considerable amount of hard work. As a result, chemical approaches have been used. Compounds such as chlorine, organic mercury compounds, chlorinated phenols, organic bromine compounds, metallic copper and organic tin and sulphur compounds have all been used in an attempt to reduce the growth of algae.

In the growing of fish in pens there is a marked need for a biodegradable antifouling coating for the nets that are used to pen the fish. The coating is required to prevent the growth of marine organisms, which restrict the flow of fresh tidal water through the net.

This need has been met by the use of antifouling coatings containing heavy metals, for example, metallic copper, organic tin and mercury compounds and the like. However, heavy metal coatings are environmentally undesirable, particularly in the marine environment because of bioaccumulation in marine life. It has been shown that they have an adverse effect upon shellfish beds and other coastal marine life, even in trace amounts. As a result, the use of heavy metals is now illegal in some jurisdictions.

In the lumber industry, wood preservatives have been used to combat fungal growth on lumber having a moisture content over 20% or which is used in marine or buried construction. Until recently, pentachlorophenols were used, but these are now regarded as environmentally unsafe. Other preservatives such as copper 8-quinolinolate, and borax-sodium carbonate mixtures have proved unsatisfactory for such reasons as poor efficacy in wet climates, rapid leaching due to high solubility and brown staining. Accordingly, there is a need to develop a coating for lumber which is effective over the long term against fungal growth.

Yet a further use of antifouling compositions is in hospitals where medically sterile environments are required if *S. aureus* infections are to be avoided, and on hard surfaces, such as, concrete.

However, no system developed so far is believed to be ideal. The prior art fails to teach coating compositions, effective over a considerable period, to destroy algae and fungi.

SUMMARY OF THE INVENTION

The object of the present invention is to provide a coating composition providing long-lasting antifouling properties. The composition comprises an emulsion polymer and a non-metallic algicide that does not react with the polymer. They are stable emulsions which can be readily applied to substrates such as fish netting, wooden shingles and lumber.

Briefly, the compositions contain partially crosslinked polymers and copolymers of vinyl compounds and from 10 to 50% by weight (based on solids) of selected quaternary ammonium compounds. The compositions, after coating, contain the quaternary ammonium compounds microencapsulated in the polymer lattices. This encapsulation of the highly soluble quaternary ammonium compounds retards their migration to the surface of the coating, thereby enabling the coating to retain biocidal activity for a long period, over one year, even in a moist or wet environment.

The compositions may contain up to 20% by weight of filler. Exemplary fillers are calcium carbonate, talc, silica and alumina. Such fillers serve to increase the bulk of the coating composition and as a carrier for the quaternary ammonium compounds.

The particularly surprising aspect of the present invention is the finding that a stable emulsion containing a substantial amount of quaternary ammonium compounds can be formed which has an almost indefinite shelf life at a temperature above 5'C. In addition, the compositions have good coating and film-forming ability as well as substantial flexibility, the latter being enhanced by the presence of the quaternary ammonium compounds.

DETAILED DESCRIPTION OF THE INVENTION

The emulsion polymers of the invention include polymers and copolymers of vinyl monomers and up to 10% by weight of acrylic monomers. Examples of the former are vinyl acetate, vinyl chloride, and vinylidene chloride.

The acrylate component may be an alpha,beta-unsaturated carboxylic acid or anhydride such as acrylic, methacrylic, and itaconic acid and anhydride; and an acrylic, an alkyl acrylate or a methacrylate ester such as ethyl acrylate, isopropyl acrylate, butyl acrylate, tertiary-butyl acrylate, 2-ethylhexyl acrylate, ethyl methacrylate, isopropyl methacrylate and isobutyl methacrylate.

As noted above, the emulsion polymers of the invention must be partially crosslinked. This crosslinking is effected via the appendent hydroxyl groups on the polymer backbone. The crosslinking must be sufficient to microencapsulate the quaternary ammonium compound. Where larger amounts of quaternary ammonium compound are desired, fillers such as precipitated silica are useful. The question of whether the crosslinking is sufficient may be readily determined by treating the composition with water and ascertaining whether the quaternary ammonium compound is leached. In order for the encapsulation to be considered satisfactory, the polymer coating must provide algicidal activity for at least one year in water at ambient temperatures.

The preferred non-metallic algicides are dialkyldimethyl ammonium compounds, preferably the chlorides and the acetates. The aforementioned compounds can be used alone or in combination with N-alkylbenzyldimethyl ammonium chloride or acetate. In both instances, there are preferably from 8 to 16 carbon atoms in each alkyl chain.

Specific examples of the dimethyldialkyl ammonium compounds are dioctyldimethyl ammonium chloride, didecyldimethyl ammonium chloride, didodecyldimethyl ammonium chloride, octyldecyldimethyl ammonium chloride, decyldodecyldimethyl ammonium acetate, and dihexadecyldimethyl ammonium acetate. Examples of the alkylbenzyldimethyl ammonium compounds are decylbenzyldimethyl ammonium chloride, decylchlorobenzyldimethyl ammonium chloride, and dodecyldichlorobenzyldimethyl ammonium acetate.

As noted above, the dialkyldimethyl ammonium compound may be used alone or in an admixture with a benzalkonium compound. The dialkyldimethyl compound may be used in admixture with up to 3.5 times as much by weight of the benzalkonium chloride. Preferably, the ratio of the benzalkonium compound to the dialkyl should be about 1:2 by weight.

In the preparation of the composition of the invention, process conditions must be carefully controlled so as to avoid the destabilization of the emulsion, that is, the coagulation of the latex particles. To achieve this result, the quaternary ammonium compound must be diluted to a solids content of not more than 50% by weight. The latex, in turn, must be diluted so that the solids concentration is less than 50%. In addition, the pH of the latex is adjusted to the alkaline range, preferably to a pH of from 6 to 11, most preferably from 8 to 9. This may readily be accomplished by the addition of alkaline material such as sodium or ammonium hydroxide, sodium carbonate, or sodium acetate. Thereafter, the diluted latex is mixed slowly for a period of from 30 min. to 1 hr. at ambient temperature.

The addition of the diluted quaternary ammonium compound to the emulsion also must be done slowly with particular care to avoid coagulation. Mixing must be done slowly during the addition and subsequently for a total of at least 5 hours. Failure to control the mixing will result in the formation of foam, excessive shear and destabilization of the latex.

If a filler is employed in the formulation, this is added to the quaternary ammonium compound prior to its introduction into the diluted latex to facillitate the absorption of the quaternary on the filler surface.

The formulation of the invention may be applied to the substrate by any of the conventional methods with the understanding that high shear should be avoided. For example, for fish net treating, dipping is employed. For other applications, dipping, spraying and brushing can be used.

In order to demonstrate more clearly the instant invention, using the procedure set forth above, the following formulations are prepared, the amounts being by weight of solids:

TABLE I

| Ingredients | 1 | 2 | 3 | 4 | 5 | 6 | 7 | 8 | 9 | 10 | A | B | C |
|---|---|---|---|---|---|---|---|---|---|---|---|---|---|
| Ethylvinylacetate (EVA) copolymer | 50 | 65 | 75 | 60 | 60 | 60 | 60 | 70 | 58.5 | 52 | 100 | 90 | 90 |
| Vinyl-acrylic copolymer | — | — | — | 5 | — | 2.5 | — | — | — | — | — | 10 | — |
| Polyvinyl chloride acrylic copolymer | — | — | — | — | 5 | 2.5 | — | — | — | — | — | — | 10 |
| Dioctyldimethyl ammonium chloride | — | — | — | — | — | — | 5 | 2.5 | 9 | 8 | — | — | — |
| Octyldecyldimethyl ammonium chloride | — | — | — | — | — | — | 10 | 5 | — | — | — | — | — |
| Didecyldimethyl ammonium chloride | 50 | 35 | 25 | 35 | 35 | 35 | 5 | 2.5 | 13.5 | 12 | — | — | — |
| N(C$_{12}$, C$_{14}$, C$_{16}$)alkyl dimethylbenzyl ammonium chloride | — | — | — | — | — | — | 20 | 20 | 9 | 8 | — | — | — |
| Filler, 1 pt CaCO$_3$, 9 pts silica | — | — | — | — | — | — | — | — | 10 | 20 | — | — | — |
| Parts of solids by weight | 100 | 100 | 100 | 100 | 100 | 100 | 100 | 100 | 100 | 100 | 100 | 100 | 100 |

FORMULATIONS

Examples 1 to 10 demonstrate preferred embodiments of the invention. In each case a stable milky emulsion is formed. After one year only a minimal amount of separation occurs. Examples A to C are comparative formulations.

EXAMPLE 1

625 g of 80% solids didecyldimethyl ammonium chloride are dissolved in 375 g of water to obtain 50% solution of quaternary ammonia.

In another vessel 893 g of latex (EVA, 56% solids, Swift Adhesive 6113, a registered trademark of Swift Adhesives) is diluted by 107 g of water to 50% emulsion. The pH of the emulsion is adjusted with ammonium to 9 and kept under continuous mixing for 30 minutes. After this time, the solution of quaternary ammonium compound is added very slowly under continuous mixing. The mixing is continuously provided for 5 hours. A stable emulsion is formed and the product is ready for use.

EXAMPLE 2

As per Example 1, except 438 g didecyldimethyl ammonium chloride is dissolved in 263 g of water and 1160 g EVA latex are diluted with 140 g of water.

EXAMPLE 3

As per Example 1, except 313 g of didecyldimethyl ammonium chloride are dissolved in 188 g of water and 1339 g of EVA latex are diluted with 161 g of water.

EXAMPLE 4

As per Example 2, except 1071 g EVA latex and 89 g vinyl-acrylic latex (UCAR 503, registered trademark of Union Carbide Corp.) are diluted with 140 g of water.

EXAMPLE 5

As per Example 4, except that 89 g of polyvinyl chloride-acrylic latex (UCAR 516, registered trademark of Union Carbide Corp.) are used instead of vinyl acrylic latex.

EXAMPLE 6

As per Example 4, except that 45 g of vinyl acrylic latex and 45 g of polyvinyl chloride-acrylic latex are used.

EXAMPLE 7

Using the process described in Example 1, 1071.3 g of EVA latex are diluted with 128.7 g of water and then blended with 250 g of ($C_8,C_{10}$) dialkyldimethyl ammonium chloride (Bardac 2080, a registered trademark of Lonza Inc.) and 250 g of ($C_{12},C_{14},C_{16}$) dialkyldimethylbenzyl ammonium chloride (Barquat MB-80, a registered trademark of Lonza Inc.). The alkyl distribution of Bardac 2080 is 1 part dioctyl, 2 parts octyldecyl and 1 part didecyl, while that fo the Barquat MB–80 is $C_{12}$-40%, $C_{14}$-50% and $C_{16}$-10%.

EXAMPLE 8

As per Example 7, except that 1249.9 g of EVA latex are diluted with 150.2 g of water, and 120 g ($C_8,C_{10}$)dialkyldimethyl ammonium chloride (Bardac 2080) and 240 g of ($C_{12},C_{14},C_{16}$)dialkyldimethylbenzyl ammonium chloride (Barquat MB-80) are used.

EXAMPLE 9

112.5 g of 80% solids dioctyldimethyl ammonium chloride, 169 g didecyldimethyl ammonium chloride and 113 g ($C_{12},C_{14},C_{16}$)dialkyldimethylbenzyl ammonium chloride are dissolved in separate vessel in 338 g of water to obtain 50% QAC solution. To this solution 100 g of precipitated silica are slowly added and mixed for 30 minutes. In another vessel 1044 g of EVA latex are diluted by 97 g of water. The process is continued as per Example 1.

EXAMPLE 10

As per Example 9, except 100 g of dioctyldimethyl ammonium chloride, 150 g didecyldimethyl ammonium chloride and 100 g ($C_{12},C_{14},C_{16}$)dialkyldimethylbenzyl ammonium chloride are dissolved in 300 g of water and 200 g of precipitated silica are used. In a second vessel 928 g of EVA latex and 86 g of water are used.

COMPARATIVE EXAMPLES

Example A 1786 g of EVA latex are diluted by 215 g of water and continuously mixed for 5 hours.

Example B 1607 g of EVA latex and 179 g of vinyl-acrylic (UCAR 503) latex are diluted by 215 g of water and continuously mixed for 5 hours.

Example C

As per Example B but, instead of vinyl-acrylic latex (UCAR 516), polyvinyl chloride-acrylic copolymer is used.

In Comparative Examples A to C, no quaternary ammonium compound is present. The emulsions are stable.

APPLICATIONS

The following Examples 11 to 15 show the application of the compositions of the invention. The results obtained are shown in Tables II to IV below.

EXAMPLE 11

Sixty-five pieces of 12"×24", 1" sq. opening, fish farm nylon 2" netting are dipped in mixtures made as per Examples 1 to 10 and A to C at 20' C. (five pieces each, dried for 2 hours at 20' C. and cured for 2 days at the same temperature). Thereafter, three pieces coated with the mixture for each of the Examples plus three uncoated pieces are submerged in the ocean in Patricia Bay, Vancouver Island, B.C., Canada; and two of each treatment and two uncoated pieces are submerged in the ocean in the Bay of Fundy, New Brunswick, Canada. The tests were commenced in mid-summer.

Tables II A and II B show the results of the treatment. The formulations of Examples A through C are emulsion polymers free of quaternary ammonium compound. The final run shows the observations on an untreated net. The results are reported in 30-day intervals for a period of one year.

TABLE IIA

| | Location: Patricia Bay B.C. Max. water temperature 22° C. | | | | | | | | | | | |
|---|---|---|---|---|---|---|---|---|---|---|---|---|
| | DAYS | | | | | | | | | | | |
| EXAMPLE | 30 | 60 | 90 | 120 | 150 | 180 | 210 | 240 | 270 | 300 | 330 | 360 |
| 1 | 0 | 0 | 0 | 0 | 0 | 0 | 0 | 0 | 0 | 1 | 1 | 2 |
| 2 | 0 | 0 | 0 | 0 | 0 | 0 | 0 | 0 | 0 | 0 | 0 | 1 |
| 3 | 0 | 0 | 0 | 0 | 0 | 0 | 0 | 0 | 0 | 0 | 1 | 2 |
| 4 | 0 | 0 | 0 | 0 | 0 | 0 | 0 | 0 | 0 | 0 | 0 | 1 |
| 5 | 0 | 0 | 0 | 0 | 0 | 0 | 0 | 0 | 0 | 0 | 0 | 1 |
| 6 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 1 |
| 8 | 0 | 0 | 0 | 0 | 0 | 0 | 0 | 0 | 0 | 1 | 2 | 2 |
| 9 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 |
| A | 3 | 4 | 5 | Completely plugged | | | | | | | | |
| B | 3 | 4 | 5 | Completely plugged | | | | | | | | |
| C | 3 | 4 | 5 | Completely plugged | | | | | | | | |

TABLE IIA-continued

Location: Patricia Bay B.C.
Max. water temperature 22° C.

| EXAMPLE | 30 | 60 | 90 | 120 | 150 | 180 | 210 | 240 | 270 | 300 | 330 | 360 |
|---------|----|----|----|-----|-----|-----|-----|-----|-----|-----|-----|-----|
| Untr. | 3 | 4 | 5 | Completely plugged | | | | | | | | |

0 — No growth
1 — Very slight growth
2 — Slight growth
3 — Growth not restricting flow of water
4 — Growth restricting flow of water
5 — Prolific growth - plugging the netting The above data clearly show the efficacy of the coating compositions of the invention in preventing the growth of algae on aquiculture fish netting.

TABLE IIB

Location: Bay of Fundy N.B.
Max. water temperature 13° C.

| EXAMPLE | 30 | 60 | 90 | 120 | 150 | 180 | 210 | 240 | 270 | 300 | 330 | 360 |
|---------|----|----|----|-----|-----|-----|-----|-----|-----|-----|-----|-----|
| 1 | 0 | 0 | 0 | 0 | 0 | 0 | 0 | 0 | 0 | 1 | 1 | 1 |
| 2 | 0 | 0 | 0 | 0 | 0 | 0 | 0 | 0 | 0 | 0 | 0 | 1 |
| 3 | 0 | 0 | 0 | 0 | 0 | 0 | 0 | 0 | 0 | 0 | 1 | 1 |
| 4 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 1 | 1 |
| 8 | 0 | 0 | 0 | 0 | 0 | 0 | 0 | 0 | 0 | 1 | 2 | 2 |
| 9 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 |
| A | 2-3 | 3-4 | 5 | Completely plugged | | | | | | | | |
| B | 3 | 4 | 5 | Completely plugged | | | | | | | | |
| C | 3 | 4 | 5 | Completely plugged | | | | | | | | |
| Untr. | 3 | 4 | 5 | Completely plugged | | | | | | | | |

0 — No growth
1 — Very slight growth
2 — Slight growth
3 — Growth not restricting flow of water
4 — Growth restricting flow of water
5 — Prolific growth - plugging the netting The above data clearly show the efficacy of the coating compositions of the invention in preventing the growth of algae on aquiculture fish netting.

EXAMPLE 12

Material from Example 1 is diluted 1 to 5 with water and sprayed over a new shake roof of one of two sheds build side by side on northern edge of the 50 ft. high forest growth in Whonnock, British Columbia. Both sheds are in full shade all year round. The second shed has an untreated shake roof made from hand cut shakes of 80 year old Western Red Cedar (second growth). Table III show the results of the experiments:

TABLE III

| | Months | | | | | | | | | | | | |
|---|---|---|---|---|---|---|---|---|---|---|---|---|---|
| | 2 | 4 | 6 | 8 | 10 | 12 | 14 | 16 | 18 | 20 | 22 | 24 | 26 | 28 |
| Treated roof | 0 | 0 | 0 | 1 | 1 | 1 | 1 | 1 | 1 | 1 | 1 | 1 | 1 | 1 |
| Untreated roof | 1 | 2 + 3 | 2 + 4 | 5 | Roof covered with algae growth | | | | | | | | | |

0 — No change of color
1 — Slight change of color
2 — Gray color
3 — Slight growth of algae (covers up to 15% of area)
4 — Growth of algae (covers up to 60% of area)
5 — Full growth of algae (covers over 80% of area)

The shake roof treated with material from Example 1, during a period of over two years, changed only slightly in 8 months. Thereafter, the color did not change for the duration of the experiment (28 months).

The untreated shake roof started to slowly change the color in the second month. At the end of the third month the color changed to greyish and the first algae growth began to show. After six months exposure to the environment, the algae growth covered approximately 55 to 60% of the area of the roof. After the eighth month, the shakes were green and soon after that, moss started to grown.

EXAMPLE 13

Part A

Materials from Example 1 to 8 and A to C are diluted 1 to 15 with water and applied to the freshly cut pieces ¼"×¾"×4" of Douglas Fir (*Pseudotauga mentiezi* Var. *Mendiezi*) wood as per ASMT D 4445-84. The wood surfaces are inoculated by the following sap stain fungi:

1) *Diplodia Natalensis P. Evans* (ATCC #34643)
2) *Caratocystis Pilifera* (ATCC #15457)
3) *Aureobasidum Pullulans* (ATCC #16624); mold fungi:

1) *Trichoderma Pseudokoningii* (ATCC #28801)
2) *Cephaloascus Fragrans* (ATCC #12091)
3) *Gliocladium Roseum* (ATCC #10521).

Part B

Materials from Examples 1 to 8 and A to C are diluted 1 to 15 with water and each material sprayed on 200 board feet of freshly cut 2"×4" lumber, marked and immediately bundled together with untreated lumber randomly placed in the bundle. Table IV shows the results of the tests described in Parts A and B:

TABLE IV

| Example | PETRI DISH - Days | | | | | | SAWMILL - Weeks | | | |
|---|---|---|---|---|---|---|---|---|---|---|
| | 30 | 60 | 90 | 120 | 150 | 180 | 8 | 14 | 20 | 26 |
| 1 | 0 | 0 | 0 | 0 | 0 | 0 | 0 | 0 | 0 | 0 |
| 2 | 0 | 0 | 0 | 0 | 0 | 1 | 0 | 0 | 0 | 0 |
| 3 | 0 | 0 | 0 | 0 | 0 | 1 | 0 | 0 | 0 | 0 |
| 4 | 0 | 0 | 0 | 0 | 0 | 1 | 0 | 0 | 0 | 0 |
| 5 | 0 | 0 | 0 | 0 | 0 | 1 | 0 | 0 | 0 | 0 |
| 6 | 0 | 0 | 0 | 0 | 0 | 0 | 0 | 0 | 0 | 0 |
| 7 | 0 | 0 | 0 | 0 | 0 | 0 | 0 | 0 | 0 | 0 |
| 8 | 0 | 0 | 0 | 0 | 1 | 2 | 0 | 0 | 1 | 1 |
| A | 5 | 5 | 5 | 5 | 5 | 5 | 5 | 5 | 5 | 5 |
| B | 5 | 5 | 5 | 5 | 5 | 5 | 5 | 5 | 5 | 5 |
| C | 5 | 5 | 5 | 5 | 5 | 5 | 5 | 5 | 5 | 5 |
| Uncoated | 5 | 5 | 5 | 5 | 5 | 5 | 5 | 5 | 5 | 5 |

0 — No discoloration, no growth
1 — single less as 1 mm spot
5 — Discoloration and green, yellow and white fungal growth.

The ASTM C 4445-84 requires 2 to 4 weeks incubation before the evaluation. Because of the excellent results with the composition of the inventions, the time and duration of the experiment was extended to 180 days. The untreated and latex treated test pieces first started showing discoloration in three days and growth of the fungi at middle of second week.

The lumber on the sawmill was first checked after three weeks. Even at that time, the untreated and latex treated surfaces which were not in contact with surface treated with solutions from Examples 1 to 8 showed unacceptable discoloration. Treated surfaces remained absolutely clear for the duration of six month experiments. This test was compared with a normal production sawmill run, where the lumber was treated with Copper 8 Quinoline compound. The latter started showing the growth in four weeks. A sawmill run with Borax sodium carbonate showed immediate change in the wood color (uneven brown) and growth of fungi in 8 weeks.

EXAMPLE 14

Two sets of 20 g of materials as per Example 1 to 10 and A to C (26 total) are poured into Petri dishes and let dry and cure for three days. After curing, the layer of material is removed from dishes and is cut to 2"×2"×1/16" pieces (4" sq.) and tested for leaching. The test pieces are initially weighed on analytical scales and the weight recorded. The test pieces are leached in continuously flowing water for twelve weeks and, during this period, periodically dried and weighed. Data is collected after the first 24 hours and then weekly during the test period. The leaching of the active ingredience, in % by weight, is calculated and reported in Table V:

TABLE V

| Example | Leaching of Active Ingredience | | | | | | | | | | | | |
|---|---|---|---|---|---|---|---|---|---|---|---|---|---|
| | 24h | 1w | 2w | 3w | 4w | 5w | 6w | 7w | 8w | 9w | 10w | 11w | 12w |
| 1 | 11.5 | 3 | 3 | 2.8 | 2.7 | 2.5 | 2.4 | 2.4 | 2.4 | 2.4 | 2.3 | 2.3 | 2.3 |
| 2 | 8 | 2.6 | 2.5 | 2.5 | 2.4 | 2.4 | 2.3 | 2.3 | 2.25 | 2.2 | 2.1 | 2.1 | 2 |
| 3 | 5 | 2.3 | 2.25 | 2.25 | 2.25 | 2.2 | 2.2 | 2.1 | 2.1 | 2 | 2 | 2 | 1.9 |
| 4 | 6.5 | 2.4 | 2.4 | 2.3 | 2.3 | 2.3 | 2.25 | 2.2 | 2.2 | 2.1 | 2 | 2 | 2 |
| 5 | 6.5 | 2.4 | 2.4 | 2.3 | 2.3 | 2.3 | 2.2 | 2.2 | 2.1 | 2.1 | 2 | 2 | 2 |
| 6 | 4.5 | 2.3 | 2.2 | 2.2 | 2.2 | 2.1 | 2.1 | 2.1 | 2.1 | 2 | 2 | 2 | 1.9 |
| 7 | 10 | 2.8 | 2.8 | 2.7 | 2.7 | 2.4 | 2.4 | 2.3 | 2.3 | 2.3 | 2.3 | 2.3 | 2.2 |
| 8 | 7 | 2.5 | 2.5 | 2.4 | 2.4 | 2.4 | 2.3 | 2.3 | 2.2 | 2.1 | 2.1 | 2 | 2 |
| 9 | 6 | 2.4 | 2.4 | 2.3 | 2.3 | 2.3 | 2.2 | 2.2 | 2.2 | 2.1 | 2 | 2 | 2 |
| 10 | 6 | 2.3 | 2.3 | 2.3 | 2.2 | 2.2 | 2.1 | 2.1 | 2.1 | 2 | 2 | 2 | 1.9 |
| A | 0 | 0 | 0 | 0 | 0.1 | 0 | 0 | 0 | 0 | 0 | 0 | 0.1 | 0 |
| B | 0 | 0 | 0 | 0 | 0 | 0 | 0.1 | 0 | 0 | 0 | 0 | 0 | 0 |
| C | 0 | 0 | 0 | 0 | 0 | 0 | 0.1 | 0 | 0 | 0 | 0 | 0 | 0 |

We claim:

1. A method of forming an antifouling composition which comprises:
   forming a first solution containing not more than 50% by weight of a non-metallic algicide consisting essentially of a dialkyldimethyl quaternary ammonium compound alone or in combination with an alkylbenzyldimethyl ammonium compound;
   forming a second solution containing less than 50% by weight of a partially crosslinked emulsion polymer selected from vinyl acetate homopolymer, vinyl acetate-acrylic copolymer, vinyl acetate-ethylene copolymer, and acrylic-polyvinyl chloride copolymer;
   adjusting the pH of said second solution to the alkaline range and thereafter stirring said second solution; and
   slowly adding said first solution to said second solution while mixing said second solution at low shear to avoid the formation of foam and the coagulation of said emulsion polymer.

2. The method of claim 1 wherein the second solution is stirred for at least 5 hours during and after the addition of the first solution.

3. The method of claim 1 wherein a filler is added to the first solution prior to admixture with the second solution.

4. A coated article which comprises a substrate coated with an antifouling coating composition comprising a partially-crosslinked polymer selected from a vinyl acetate homopolymer; a vinyl acetate-acrylic copolymer; a vinyl acetate-ethylene copolymer; and an acrylic-polyvinyl chloride copolymer; and
   a non-metallic algicide consisting essentially of a quaternary ammonium compound having methyl groups and two alkyl groups alone or in combination with a second quaternary ammonium compound having methyl groups, an alkyl group and a benzyl group, said algicide being encapsulated in said polymer and being capable of being leeched from said composition during submersion.

5. The coated article of claim 4 wherein the coated article is a fish net or buoy.

6. The coated article of claim 4 wherein the substrate is a porous article.

7. The coated article of claim 6 wherein the substrate is wood or concrete.

* * * * *